(12) United States Patent
Shenai-Khatkhate et al.

(10) Patent No.: US 7,531,458 B2
(45) Date of Patent: May 12, 2009

(54) ORGANOMETALLIC COMPOUNDS

(75) Inventors: Deodatta Vinayak Shenai-Khatkhate, Danvers, MA (US); Qing Min Wang, North Andover, MA (US)

(73) Assignee: Rohm and Haas Electronics Materials LLP, Marlborough, MA (US)

( * ) Notice: Subject to any disclaimer, the term of this patent is extended or adjusted under 35 U.S.C. 154(b) by 308 days.

(21) Appl. No.: 11/540,072

(22) Filed: Sep. 29, 2006

(65) Prior Publication Data
US 2008/0026578 A1 Jan. 31, 2008

Related U.S. Application Data

(60) Provisional application No. 60/834,478, filed on Jul. 31, 2006.

(51) Int. Cl.
*H01L 21/44* (2006.01)
*C23C 16/00* (2006.01)
*C07F 5/00* (2006.01)

(52) U.S. Cl. .................... 438/681; 438/680; 556/1; 556/18; 556/20; 556/43; 556/52; 556/53; 118/715; 106/1.25; 427/248.1

(58) Field of Classification Search ............ 556/18, 556/20, 1, 43, 52, 53; 438/680, 681; 427/248.1; 106/1.25; 118/715
See application file for complete search history.

(56) References Cited

FOREIGN PATENT DOCUMENTS

| EP | 1 059 296 | 12/2000 |
|---|---|---|
| EP | 1 531 191 | 5/2005 |
| EP | 1 566 835 | 8/2005 |
| WO | WO 2005/112101 A2 | 11/2005 |

OTHER PUBLICATIONS

European Search Report of corresponding European Application No. 07 11 3255.9.
Jakschitz et al.; Monolithic poly [(trimethylsilyl-4-methylstyrene)-co-b is (4-vinylbenzyl)dimethylsilane] stationary phases for the fast separation of proteins and oligonucleotides; Journal of Chromatography, A, 1147(1); 2007; pp. 53-58.
Yuan et al.; "Synthesis and Second-Order NLO Properties of Donor-Acceptor .sigma.-Alkenyl Ruthenium Complexes"; Organometallics, 26(1); 2007; pp. 196-200.
Wilton-Ely et al; "Spectroscopic, structural and theoretical investigation of alkenyl ruthenium complexes supported by sulfur-nitrogen mixed-donor ligands"; European Journal of Inorganic Chemistry, (15); 2006; pp. 3068-3078.
Wilton-Ely et al.; ".sigma.-Organyl complexes of ruthenium and osmium supported by a mixed-donor ligand"; Dalton Transactions, (11); 2005; pp. 1930-1939.
Hill et al.; "The sting of the 1-4,6 scorpion: a metallaboratrane"; Angewandte Chemie, International Edition, 38(18); 1999; pp. 2759-2761.
Yi et al.; "Catalytic Synthesis of Tricyclic Quinoline Derivatives from the Regioselective Hydroamination and C-H Bond Activation Reaction of Benzocyclic Amines and Alkynes"; Journal of The American Chemical Society, 127(16); 2005; pp. 5782-5783.
Jung et al.; "A series of vinylidene-, vinyl-, carbine- and carbyneruthenium (II) complexes with [Ru(PCy3)2] and [Ru(PiPr3)2] as molecular building blocks"; European Journal of Inorganic Chemistry, (3); 2004; pp. 469-480.
Liu et al.; "Synthesis of [TpRu(CO)(PPh3)]2(.mu.-CH:CH-CH:Ch-C6H4-CH:CH-CH:CH) from Wittig reactions"; Journal of Organometallic Chemistry, 683(2); 2003; pp. 331-336.
Maruyama et al.; "Mechanisms of C-Si and C-H Bond Formation on the Reactions of Alkenylruthenium (II) Complexes with Hydrosilanes"; Organometallics, 19(7); 2000; pp. 1308-1318.
Santos et al.; "The Effect of N-Donor Ligands on the Reaction of N-Donor Ligands on the Reaction of Ruthenium Hydrides with 1-Alkynes"; Organometallics, 16(15); 1997; pp. 3482-3488.
Jia et al.; "Reactions of RuHCl (CO)(PPh3 with 1-alkynols. Preparation and reactivity of hydroxyvinyl complexes"; Journal of Organometallic Chemistry, 538(1-2); 1997; pp. 31-40.
Cunha et al.; "Selectivity aspects of the ring opening reaction of 2-alkenyl aziridines by carbon nucleophiles"; Tetrahedron Letters, 46(15); 2005; pp. 2539-2542.
Huang et al.; "Telluro-directed regiospecific and highly stereoselective reaction of ethyl 5-tellujro-(2E, 4Z)-pentadienoate with organocopper reagents"; Tetrahedron Letters, 39(5/6); 1998; pp. 419-422.
Kuniyasu et al.; "The first definitive example of oxidative addition of acyclic vinyl selenide to M(O) complex"; Journal of Organometallic Chemistry, 691(9); 2006; pp. 1873-1878.
Ohtaka et al.; "Photo-and-Thiol-Driven Trans Insertion of Phenylacetylene into H-PT Bonds"; Journal of the American Chemical Society, 124(48); 2002; pp. 14324-14325.
Chen et al.; "Synthesis of (+)-CP-263, 114"; Journal of the American Chemical Society, 122(30); 2000; pp. 7424-7425.
Comins et al.; "Asymmetric synthesis of dienomycin C"; Tetrahedron Letters, 40(2); 1999; pp. 217-218.
Satoh et al.; "Magnesium alkylidene carbenoids: generation from 1-halovinyl sulfoxides with Grignard reagents and studies on their properties, mechanism, and som synthetic uses"; Tetrahedron, 54(21); 1998; pp. 5557-5574.
Takuwa et al.; "Photochemical 1,3-stannyl rearrangement of allylic stannanes"; Journal of the Chemical Society, Perkin Transactions 1: Organic and Bio-Organic Chemistry, (7); 1998; pp. 1309-1314.
Araki et al.; "Regioselective allylation and alkylation of electron-deficient alkenes with organogallium and organoindium reagents"; Tetrahedron Letters, 40(12); 1999; pp. 2331-2334.

*Primary Examiner*—Porfirio Nazario Gonzalez
(74) *Attorney, Agent, or Firm*—S. Matthew Cairns

(57) ABSTRACT

Organometallic compounds containing an electron donating group-substituted alkenyl ligand are provided. Such compounds are particularly suitable for use as vapor deposition precursors. Also provided are methods of depositing thin films, such as by ALD and CVD, using such compounds.

9 Claims, No Drawings

ORGANOMETALLIC COMPOUNDS

This application claims the benefit of U.S. Provisional Application Ser. No. 60/834,478, filed on Jul. 31, 2006.

The present invention relates generally to the field of organometallic compounds. In particular, the present invention relates to the field of organometallic compounds useful for chemical vapor deposition or atomic layer deposition of thin films.

In atomic layer deposition ("ALD") processes, conformal thin films are deposited by exposing a surface to alternating vapors of two or more chemical reactants. Vapor from a first precursor (or reactant) is brought to the surface onto which the desired thin film is to be deposited. Any unreacted vapor is then removed from the system under vacuum. Next, vapor from a second precursor is brought to the surface and allowed to react with the first precursor, with any excess second precursor vapor being removed. Each step in the ALD process typically deposits a monolayer of the desired film. This sequence of steps is repeated until the desired film thickness is obtained. In general, ALD processes are performed at fairly low temperatures, such as from 200 to 400° C. The exact temperature range will depend on the particular film to be deposited as well as on the particular precursors employed. ALD processes have been used to deposit pure metals as well as metal oxides, metal nitrides, metal carbide nitrides, and metal silicide nitrides.

ALD precursors must be sufficiently volatile to ensure a sufficient concentration of the precursor vapor in the reactor to deposit a monolayer on the substrate surface within a reasonable period of time. The precursors must also be sufficiently stable to be vaporized without premature decomposition and unwanted side reactions, but must also be sufficiently reactive to form the desired film on the substrate. With such a required balance of volatility and stability properties, there is an overall lack of suitable precursors.

Conventional precursors are homoleptic, i.e. they have a single ligand group. Homoleptic precursors offer uniform chemical characteristics, thus offering the inherent advantage of matching and harmonizing the functionality of ligand with the deposition process. However, the use of only a single ligand group offers less control over other paramount precursor characteristics, such as the shielding of metal center, that governs the surface reactions (e.g. chemisorption) and gas phase reaction (e.g. reaction with second complementary precursor), adjusting the volatility of precursor, and achieving required thermal stability for the precursor. For example, tetrakis(dialkylamino)hafnium is currently used as a chloride-free alternative to $HfCl_4$. However, members of this class of compound tend to prematurely decompose during the storage and/or before reaching the reactor. Substituting one or more of the dialkylamino groups with another organic group that imparts thermal stability has been tried but with little success, due to the inability to match the functionality of other group and achieve the desired stability. Certain alkenyl-substituted Group 14 compounds are disclosed as vapor deposition precursors for metalorganic chemical vapor deposition ("MOCVD") in U.S. Patent Application No. 2004/0194703 (Shenai-Khatkhate et al.). Such compounds may not provide the balance of volatility and thermal stability (or other properties) needed under certain ALD conditions. There remains a need for suitable and stable precursors that meet the deposition requirements and produce films that are essentially carbon-free.

The present invention provides an organometallic compound having the formula $(EDG\text{-}(CR^1R^2)_{y'}\text{---}CR^3\text{=}CR^4\text{---}(CR^5R^6)_{y''})_n M^{+m} L^1_{(m-n)} L^2_p$, wherein each $R^1$ and $R^2$ are independently chosen from H, $(C_1\text{-}C_6)$alkyl and EDG; $R^3$=H, $(C_1\text{-}C_6)$alkyl, EDG or EDG-$(CR^1R^2)_{y'}$; $R^4$=H or $(C_1\text{-}C_6)$alkyl; each $R^5$ and $R^6$ are independently chosen from H and $(C_1\text{-}C_6)$alkyl; EDG is an electron donating group; M=a metal; $L^1$=an anionic ligand; $L^2$ is a neutral ligand; y'=0-6; y"=0-6; m=the valence of M; n=1-7; and p=0-3. Such compounds are suitable for use as precursors in a variety of vapor deposition methods, such as chemical vapor deposition ("CVD") and MOCVD in particular, and are particularly suitable for ALD. Also provided is a composition including the above described organometallic compound and an organic solvent. Such a composition is particularly suitable for use in ALD and direct liquid injection processes.

The present invention further provides a method of depositing a film including the steps of: providing a substrate in a reactor; conveying the organometallic compound described above in a gaseous form to the reactor; and depositing a film including the metal on the substrate. In another embodiment, the present invention provides a method of depositing a film including the steps of: providing a substrate in a reactor; conveying as a first precursor the organometallic compound described above in a gaseous form to the reactor; chemisorbing the first precursor compound on the surface of the substrate; removing any non-chemisorbed first precursor compound from the reactor; conveying a second precursor in a gaseous form to the reactor; reacting the first and second precursors to form a film on the substrate; and removing any unreacted second precursor.

As used throughout this specification, the following abbreviations shall have the following meanings, unless the context clearly indicates otherwise: ° C.=degrees centigrade; ppm=parts per million; ppb=parts per billion; RT=room temperature; M=molar; Me=methyl; Et=ethyl; i-Pr=iso-propyl; t-Bu=tert-butyl; c-Hx=cyclohexyl; Cp=cyclopentadienyl; Py=pyridyl; COD=cyclooctadiene; CO=carbon monoxide; Bz=benzene; Ph=phenyl; VTMS=vinyltrimethylsilane; and THF=tetrahydrofuran.

"Halogen" refers to fluorine, chlorine, bromine and iodine and "halo" refers to fluoro, chloro, bromo and iodo. Likewise, "halogenated" refers to fluorinated, chlorinated, brominated and iodinated. "Alkyl" includes linear, branched and cyclic alkyl. Likewise, "alkenyl" and "alkynyl" include linear, branched and cyclic alkenyl and alkynyl, respectively. The articles "a" and "an" refer to the singular and the plural.

Unless otherwise noted, all amounts are percent by weight and all ratios are molar ratios. All numerical ranges are inclusive and combinable in any order except where it is clear that such numerical ranges are constrained to add up to 100%.

The organometallic compounds of the present invention have the general formula $(EDG\text{-}(CR^1R^2)_{y'}\text{---}CR^3\text{=}CR^4\text{---}(CR^5R^6)_{y''})_n M^{+m} L^1_{(m-n)} L^2_p$, wherein each $R^1$ and $R^2$ are independently chosen from H, $(C_1\text{-}C_6)$alkyl and EDG; $R^3$=H, $(C_1\text{-}C_6)$alkyl, EDG or EDG-$(CR^1R^2)_{y'}$; $R^4$=H or $(C_1\text{-}C_6)$ alkyl; each $R^5$ and $R^6$ are independently chosen from H and $(C_1\text{-}C_6)$alkyl; EDG is an electron donating group; M=a metal; $L^1$=an anionic ligand; $L^2$ is a neutral ligand; y'=0-6; y"=0-6; m=the valence of M; n=1-7; and p=0-3. In the formula, m≧n. In one embodiment, y'=0-3. In another embodiment, y"=0-3. In a further embodiment, y"=0-2, and in a still further embodiment, y"=0. The subscript "n" represents the number of EDG-substituted alkenyl ligands in the present compounds. The valence of M is typically 2-7 (i.e., typically m=2-7), more typically 3-7, and still more typically 3-6. In one embodiment, each $R^1$-$R^6$ is independently chosen from H, methyl, ethyl, propyl, butyl, and an electron donating group ("EDG"), and more particularly H, methyl, ethyl and propyl. In another embodiment, each of $R^4$, $R^5$ and $R^6$ is independently chosen from H and $(C_1-C_3)$alkyl. In yet another embodiment, $R^3$=EDG-$(CR^1R^2)_{y'}$. In one embodiment, $(m-n) \geq 1$, i.e. the organometallic compound is heteroleptic.

A wide variety of metals may suitably be used to form the present organometallic compounds. Typically, M is chosen from a Group 2 to Group 16 metal. As used herein, the term "metal" includes the metalloids boron, silicon, arsenic, selenium and tellurium but does not include carbon, nitrogen, phosphorus, oxygen and sulfur. In one embodiment, M=Be, Mg, Sr, Ba, Al, Ga, In, Si, Ge, Sb, Bi, Se, Te, Po, Cu, Zn, Sc, Y, La, a lanthanide metal, Ti, Zr, Hf, Nb, W, Mn, Co, Ni, Ru, Rh, Pd, Ir or Pt. In another embodiment, M=Al, Ga, In, Ge, La, a lanthanide metal, Ti, Zr, Hf, Nb, W, Mn, Co, Ni, Ru, Rh, Pd, Ir or Pt.

Suitable electron donating groups for EDG are any which provide π-electron stabilization to the metal. The electron donating groups may be any which include one or more of oxygen, phosphorus, sulfur, nitrogen, alkenes, alkynes and aryl groups. Salts of electron donating groups, such as their alkali or alkaline earth metal salts, may also be used. Exemplary electron donating groups include, without limitation, hydroxyl ("—OH"), $(C_1-C_6)$alkoxy ("—OR"), carbonyl ("—C(O)—"), carboxy ("—CO$_2$X"), carb$(C_1-C_6)$alkoxy ("—CO$_2$R"), carbonate ("—OCO$_2$R"), amino ("—NH$_2$"), $(C_1-C_6)$alkylamino ("—NHR"), di$(C_1-C_6)$alkylamino ("—NR$_2$"), $(C_2-C_6)$alkenylamino, di$(C_2-C_6)$alkenylamino, $(C_2-C_6)$alkynylamino, di$(C_2-C_6)$alkynylamino, mercapto ("—SH"), thioethers ("—SR"), thiocarbonyl ("—C(S)—"), phosphono ("PH$_2$"), $(C_1-C_6)$alkylphosphino ("—PHR"), di$(C_1-C_6)$alkylphosphino ("—PR$_2$"), vinyl ("C=C"), acetylenyl ("C≡C"), pyridyl, phenyl, furanyl, thiophenyl, aminophenyl, hydroxyphenyl, $(C_1-C_6)$alkylphenyl, di$(C_1-C_6)$ alkylphenyl, $(C_1-C_6)$alkylphenol, $(C_1-C_6)$alkoxy-$(C_1-C_6)$ alkylphenyl, biphenyl and bipyridyl. The electron donating group may include another electron donating group, as in hydroxyphenyl, aminophenyl and alkoxyphenyl. In one embodiment, the EDG is selected from amino, $(C_1-C_6)$alkylamino, di$(C_1-C_6)$alkylamino, $(C_2-C_6)$alkenylamino, di$(C_2-C_6)$alkenylamino, $(C_2-C_6)$alkynylamino, and di$(C_2-C_6)$alkynylamino. In a further embodiment, the EDG is selected from NH$_2$, methylamino, dimethylamino, ethylamino, diethylamino, ethylmethylamino, di-iso-propylamino, methyl-iso-propylamino, allylamino, diallylamino, propargylamino and dipropargylamino. In yet a further embodiment, the EDG is an aryl moiety, and more particularly an aromatic heterocycle such as pyridine.

A wide variety of anionic ligands ($L^1$) may be used in the present invention. Such ligands bear a negative charge. Possible ligands include, without limitation: hydride, halide, azide, alkyls, alkenyl, alkynyl, carbonyl, dialkylaminoalkyl, imino, hydrazido, phosphido, nitrosyl, nitryl, nitrite, nitrate, nitrile, alkoxy, dialkylaminoalkoxy, siloxy, diketonates, ketoiminates, cyclopentadienyls, silyls, pyrazolates, guanidinates, phosphoguanidinates, amidinates, phosphoamidinates, amino, alkylamino, dialkylamino and alkoxyalkyldialkylamino. Any of such ligands may be optionally substituted such as by replacing one or more hydrogens with another substituent group such as halo, amino, disilylamino and silyl. Exemplary anionic ligands include, but are not limited to: $(C_1-C_{10})$alkyl such as methyl, ethyl, propyl, butyl, pentyl, hexyl, cyclopropyl, cyclopentyl and cyclohexyl; $(C_2-C_{10})$alkenyl such as ethenyl, allyl, and butenyl; $(C_2-C_{10})$alkynyl such as acetylenyl and propynyl; $(C_1-C_{10})$alkoxy such as methoxy, ethoxy, propoxy, and butoxy; cyclopentadienyls such as cyclopentadienyl, methylcyclopentadienyl and pentamethylcyclopentadienyl; di$(C_1-C_{10})$alkylamino$(C_1-C_{10})$alkoxy such as dimethylaminoethoxy, diethylaminoethoxy, dimethylaminopropoxy, ethylmethylaminopropoxy and diethylaminopropoxy; silyls such as $(C_1-C_{10})$alkylsilyls and $(C_1-C_{10})$alkylaminosilyls; alkyl amidinates such as N,N'-dimethyl-methylamidinato, N,N'diethyl-methylamidinato, N,N'-diethyl-ethylamidinato, N,N'-di-iso-propyl-methylamidinato, N,N'-di-iso-propyl-iso-propylamidinato, N,N'-dimethyl-phenylamidinato; $(C_1-C_{10})$alkylamino such as methylamino, ethylamino, and propylamino; di$(C_1-C_{10})$ alkylamino such as dimethylamino, diethylamino, ehtylmethylamino and dipropylamino; $(C_2-C_6)$alkenylamino; di$(C_2-C_6)$alkenylamino such as diallylamino; $(C_2-C_6)$alkynylamino such as propargylamino; and di$(C_2-C_6)$alkynylamino such as dipropargylamino. When 2 or more $L^1$ ligands are present, such ligands may be the same or different, i.e. the $L^1$ ligands are independently selected. In one embodiment, at least one $L^1$ ligand is present.

Neutral ligands ($L^2$) are optional in the present compounds. Such neutral ligands do not bear an overall charge and may function as stabilizers. Neutral ligands include, without limitation, CO, NO, alkenes, dienes, trienes, alkynes, and aromatic compounds. Exemplary neutral ligands include, but are not limited to: $(C_2-C_{10})$alkenes such as ethene, propene, 1-butene, 2-butene, 1-pentene, 2-pentene, 1-hexene, 2-hexene, norbornene, vinylamine, allylamine, vinyltri$(C_1-C_6)$ alkylsilane, divinyldi$(C_1-C_6)$alkylsilane, vinyltri$(C_1-C_6)$ alkoxysilane and divinyldi$(C_1-C_6)$alkoxysilane; $(C_4-C_{12})$ dienes such as butadiene, cyclopentadiene, isoprene, hexadiene, octadiene, cyclooctadiene, norbornadiene and α-terpinene; $(C_6-C_{16})$trienes; $(C_2-C_{10})$alkynes such as acetylene and propyne; and aromatic compounds such as benzene, o-xylene, m-xylene, p-xylene, toluene, o-cymene, m-cymene, p-cymene, pyridine, furan and thiophene. The number of neutral ligands depends upon the particular metal chosen for M. Typically, the number of neutral ligands is from 0-3. When 2 or more neutral ligands are present, such ligands may be the same or different.

The present organometallic compounds may be prepared by a variety of methods known in the art. For example, EDG-substituted alkenyl Grignards may be reacted with a metal halide in a suitable solvent such as an ethereal solvent like THF or diethyl ether to form the present EDG-substituted alkenyl organometallic compounds. Alternatively, EDG-substituted alkenyllithium compounds may be reacted with a suitable metal reactant such as a metal halide, metal acetate or metal alkoxide, in a suitable solvent such as hexane to form the desired EDG-substituted alkenyl organometallic compound.

The above-described organometallic compounds are particularly suitable for use as precursors for the vapor phase deposition of thin films. Such compounds may be used in a variety of CVD processes as well as in a variety of ALD processes. In one embodiment, 2 or more of such organometallic compounds may be used in a CVD or ALD process. When 2 or more organometallic compounds are used, such compounds may contain the same metal but having different ligands, or may contain different metals. In another embodiment, one or more of the present organometallic compounds may be used with one or more other precursor compounds.

Bubblers (also known as cylinders) are the typical delivery devices used to provide the present organometallic compounds in the vapor phase to a deposition reactor. Such bubblers typically contain a fill port, a gas inlet port and an outlet port which is connected to a vaporizer that is connected to a deposition chamber if direct liquid injection is employed. The outlet port may be directly connected to a deposition chamber. A carrier gas typically enters the bubbler through the gas inlet port and entrains or picks up precursor vapor or a precursor-containing gas stream. The entrained or carried vapor then exits the bubbler through the outlet port and is conveyed to the deposition chamber. A variety of carrier gases may be used, such as hydrogen, helium, nitrogen, argon and mixtures thereof.

A wide variety of bubblers may be used, depending upon the particular deposition apparatus used. When the precursor compound is a solid, the bubblers disclosed in U.S. Pat. No. 6,444,038 (Rangarajan et al.) and U.S. Pat. No. 6,607,785 (Timmons et al.), as well as other designs, may be used. For liquid precursor compounds, the bubblers disclosed in U.S. Pat. No. 4,506,815 (Melas et al) and U.S. Pat. No. 5,755,885 (Mikoshiba et al) may be used, as well as other liquid precursor bubblers. The source compound is maintained in the bubbler as a liquid or solid. Solid source compounds are typically vaporized or sublimed prior to transportation to the deposition chamber. Bubbler for use with ALD processes may have pneumatic valves at the inlet and outlet ports to facility opening and closing rapidly as required to provide the necessary vapor pulses.

In conventional CVD processes, a bubbler for supplying a liquid precursor, as well as certain bubblers for supplying solid precursors, will contain a dip tube which is connected to the gas inlet port. In general, the carrier gas is introduced below the surface of the organometallic compound, also called a precursor or source compound, and travels upward through the source compound to the headspace above it, entraining or carrying vapor of the source compound in the carrier gas.

Precursors used in ALD processes are often liquids, low melting solids, or solids formulated in a solvent. To handle these types of precursors, bubblers used in ALD processes may contain a dip tube connected to the outlet port. Gas enters these bubblers through the inlet, pressurizes the bubbler and forces the precursor up the dip tube and out of the bubbler.

The present invention provides a delivery device including the organometallic compound described above. In one embodiment, the delivery device includes a vessel having an elongated cylindrical shaped portion having an inner surface having a cross-section, a top closure portion and a bottom closure portion, the top closure portion having an inlet opening for the introduction of a carrier gas and an outlet opening, the elongated cylindrical shaped portion having a chamber containing the organometallic compound described above.

In an embodiment, the present invention provides a device for feeding a fluid stream saturated with an organometallic compound of the formula $(EDG\text{-}(CR^1R^2)_{y'}\text{-}CR^3{=}CR^4\text{-}(CR^5R^6)_{y''})_n M^{+m} L^1_{(m-n)} L^2_p$, wherein each $R^1$ and $R^2$ are independently chosen from H, $(C_1\text{-}C_6)$alkyl and EDG; $R^3{=}H$, $(C_1\text{-}C_6)$alkyl, EDG or $EDG\text{-}(CR^1R^2)_{y'}$; $R{=}H$ or $(C_1\text{-}C_6)$alkyl; each $R^5$ and $R^6$ is independently chosen from H and $(C_1\text{-}C_6)$alkyl; EDG is an electron donating group; M=a metal; $L^1$=an anionic ligand; $L^2$ is a neutral ligand; y'=0-6; y''=0-6; m=the valence of M; n=1-7; and p=0-3 to a chemical vapor deposition system including a vessel having an elongated cylindrical shaped portion having an inner surface having a cross-section, a top closure portion and a bottom closure portion, the top closure portion having an inlet opening for the introduction of a carrier gas and an outlet opening, the elongated cylindrical shaped portion having a chamber containing the organometallic compound; the inlet opening being in fluid communication with the chamber and the chamber being in fluid communication with the outlet opening. In a still further embodiment, the present invention provides an apparatus for chemical vapor deposition of metal films including one or more devices for feeding a fluid stream saturated with the organometallic compound described above.

The deposition chamber is typically a heated vessel within which is disposed at least one, and possibly many, substrates. The deposition chamber has an outlet, which is typically connected to a vacuum pump in order to draw by-products out of the chamber and to provide a reduced pressure where that is appropriate. MOCVD can be conducted at atmospheric or reduced pressure. The deposition chamber is maintained at a temperature sufficiently high to induce decomposition of the source compound. The typical deposition chamber temperature is from 200° to 1200° C., more typically 200-600° C., the exact temperature selected being optimized to provide efficient deposition. Optionally, the temperature in the deposition chamber as a whole can be reduced if the substrate is maintained at an elevated temperature, or if other energy such as plasma is generated by an radio frequency ("RF") source.

Suitable substrates for deposition, in the case of electronic device manufacture, may be silicon, silicon germanium, silicon carbide, gallium nitride, gallium arsenide, indium phosphide, and the like. Such substrates are particularly useful in the manufacture of integrated circuits.

Deposition is continued for as long as desired to produce a film having the desired properties. Typically, the film thickness will be from several hundred to several thousand angstroms or more when deposition is stopped.

Thus, the present invention provides a method for depositing a metal film including the steps of: a) providing a substrate in a vapor deposition reactor; b) conveying as a precursor the organometallic compound described above is a gaseous form to the reactor; and c) depositing a film including the metal on the substrate. In a typical CVD process, the above described method further includes the step of decomposing the precursor in the reactor.

Thin metal-containing films are produced by ALD with almost perfect stoichiometry by alternately subjecting the substrate, one at a time, to the vapor of precursor compounds of each of the elements of which the film is formed. In ALD processes, a substrate is subjected to the vapor of a first precursor which can react with the surface of the substrate at a temperature sufficiently high for such reaction to occur whereby a single atomic layer of the first precursor (or metal contained therein) is formed on the surface of the substrate, and subjecting the thus formed surface with the first precursor atomic layer thereon to the vapor of a second precursor which reacts with the first precursor at a temperature sufficiently high for such reaction to occur whereby a single atomic layer of the desired metal film is formed on the surface of the substrate. This procedure can be continued by alternately using the first and second precursors until the film that is formed reaches a desire to thickness. The temperatures used in such ALD processes are typically lower than those employed in MOCVD process and may be in the range of 200 to 400° C., although other suitable temperatures may be employed depending upon the precursors chosen, the film to be deposited, and on other criteria known to those skilled in the art.

An ALD apparatus typically includes a vacuum chamber means to provide an evacuated atmosphere, a pair of means situated in the vacuum chamber means, the pair of means including a support means for supporting at least one substrate and a source means for forming sources for as least two vapors of two different precursors, respectively, and operating means operatively connected with one of the pair of means for operating the one means with respect to the other of the pair of means for providing on the substrate first a single atomic layer of one of the precursors and then a single atomic layer of the other precursor. See, e.g., U.S. Pat. No. 4,058,430 (Suntola) for a description of an ALD apparatus.

In a further embodiment, the present invention provides a method of depositing a film including the steps of: providing a substrate in a vapor deposition reactor; conveying as a first precursor the organometallic compound described above in a gaseous form to the reactor; chemisorbing the first precursor compound on the surface of the substrate; removing any non-chemisorbed first precursor compound from the reactor; conveying a second precursor in a gaseous form to the reactor; reacting the first and second precursors to form a film on the substrate; and removing any unreacted second precursor. The alternating steps of conveying the first and second precursors and step of reacting the first and second precursors being repeated until a film of the desired thickness is obtained. The step of removing a precursor from the reactor may include one or more of evacuating the reactor under vacuum and purging the reactor using a non-reactant gas. The second precursor may be any suitable precursor that reacts with the first precursor to form the desired film. Such second precursors may optionally contain another metal. Exemplary second precursors include, but are not limited to, oxygen, ozone, water, hydrogen peroxide, alcohols, nitrous oxide and ammonia.

When the present organometallic compounds are to be used in ALD processes or in direct liquid injection processes, they may be combined with an organic solvent. Mixtures of organic solvents may be employed. Any organic solvent which is suitably inert to the organometallic compound can be used. Exemplary organic solvents include, without limitation, aliphatic hydrocarbons, aromatic hydrocarbons, linear alkyl benzenes, halogenated hydrocarbons, silyated hydrocarbons, alcohols, ethers, glymes, glycols, aldehydes, ketones, carboxylic acids, sulphonic acids, phenols, esters, amines, alkylnitrile, thioethers, thioamines, cyanates, isocyanates, thiocyanates, silicone oils, nitroalkyl, alkylnitrate, and mixtures thereof. Suitable solvents include tetrahydrofuran, diglyme, n-butyl acetate, octane, 2-methoxyethyl acetate, ethyl lactate, 1,4-dioxane, vinyltrimethylsilane, pyridine, mesitylene, toluene, and xylene. When used in direct liquid injection processes, the concentration of the organometallic compound is typically in the range of 0.05 to 0.25 M, and more typically 0.05 to 0.15 M. The organometallic compound/organic solvent compositions may be in the form of solutions, slurries or dispersions.

Compositions including the present organometallic compound and an organic solvent are suitable for use in vapor deposition processes employing direct liquid injection. Suitable direct liquid injection processes are those described in U.S. Patent Application No. 2006/0110930 (Senzaki).

Further provided by the present invention is a method for manufacturing an electronic device including the step of depositing a metal-containing film using any one of the above described methods.

The present invention provides an enabling solution to the use of heteroleptic precursors for vapor deposition, particularly ALD, which have a suitable balance of functionality, desired thermal stability, appropriate metal center shielding and well governed surface as well as gas phase reactions, by use of the EDG-substituted alkenyl ligands.

The following examples are expected to illustrate various aspects of the present invention.

EXAMPLE 1

(1-Dimethylamino)allyl(η6-p-cymene)ruthenium diisopropylacetamidinate is expected to be synthesized as follows:

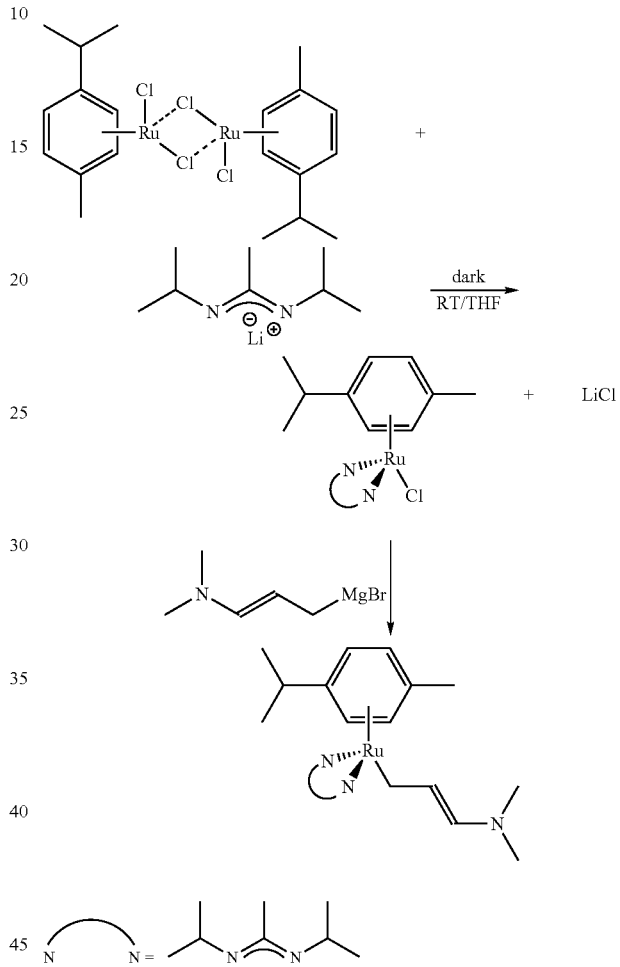

Dichloro(η6-p-cymene)ruthenium dimer is reacted with lithium diisopropylacetamidinate in THF at room temperature (approximately 25° C.) in a 3-neck round bottom flask which is equipped with magnetic or mechanical stirring and effective heating/cooling system to control the rate of reaction. After the mixture is stirred overnight at room temperature, (1-dimethylamino)allyl magnesium bromide is added at low temperature (approximately −30° C.). The resulting mixture is then stirred overnight under an inert atmosphere of nitrogen. The reagents are added in continuous and dropwise manner, and are allowed to mix slowly to control the exothermicity of the reaction. The crude product is then expected to separate from the reaction mass after filtration with a high yield expected. The target product is expected to be substantially free of organic solvents (<0.5 ppm) as determined by FT-NMR and also substantially free of metallic impurities (<10 ppb) as determined by ICP-MS/ICP-OES.

EXAMPLE 2

Bis(1-dimethylaminoallyl)bis(cyclopentadienyl)zirconium (IV) is expected to be synthesized as:

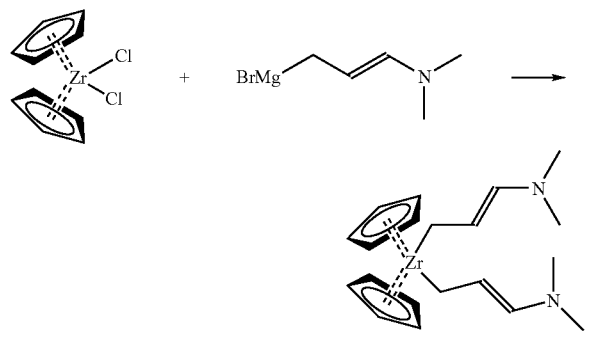

Dichloro bis(cyclopentadiene)zirconium is reacted with (1-dimethylamino)allyl magnesium bromide in THF at a low temperature (approximately −30° C.) in a 3-neck round bottom flask which is equipped with magnetic or mechanical stirring and effective heating/cooling system to control the rate of reaction. The mixture is stirred overnight at room temperature. The crude product is then expected to separate from the reaction mass after filtration with a high yield expected. The target product is expected to be substantially free of organic solvents (<0.5 ppm) as determined by FT-NMR and also substantially free of metallic impurities (<10 ppb) as determined by ICP-MS/ICP-OES.

EXAMPLE 3

Organometallic compounds of the formula $(EDG-(CR^1R^2)_{y'}-CR^3=CR^4-(CR^5R^6)_{y''})_n M^{+m} L^1_{(m-n)} L^2_p$ listed in the following table are expected to be prepared according to the procedures described in Examples 1 or 2.

EXAMPLE 4

Compositions suitable for use in ALD or direct liquid injection processes are prepared by combining certain of the compounds of Example 3 with certain organic solvents. The particular compositions are shown in the following table. The organometallic compounds are typically present in a concentration of 0.1 M for direct liquid injection.

| Composition Sample | Organometallic Compound Sample | Solvent |
|---|---|---|
| 1 | C | 1,4-Dioxane |
| 2 | D | THF |
| 3 | D | 2-Methoxyethyl acetate |
| 4 | E | Diglyme |
| 5 | F | THF |
| 6 | G | n-Butyl acetate |
| 7 | H | Diglyme |
| 8 | H | Octane |
| 9 | H | Diglyme/THF |
| 10 | I | n-Butyl acetate |
| 11 | I | Octane |
| 12 | I | 2-Methoxyethoxy acetate |
| 13 | J | THF |
| 14 | K | Octane |
| 15 | K | Diglyme |
| 16 | L | n-Butyl acetate |
| 17 | M | 2-Methoxyethoxy acetate |
| 18 | N | Octane |
| 19 | N | THF |
| 20 | P | 2-Methoxyethoxy acetate |
| 21 | P | Octane |

What is claimed is:
1. A method of depositing a film comprising the steps of: providing a substrate in a reactor; conveying a composition comprising an organometallic compound having the formula

| Sample | M | n | EDG | y'/y'' | $R^1/R^2$ | $R^3/R^4$ | $R^5/R^6$ | $L^1$ | $L^2$ |
|---|---|---|---|---|---|---|---|---|---|
| A | Mg | 1 | $NMe_2$ | 0/1 | — | H/H | H/H | OEt | — |
| B | Ga | 1 | N(Et)Me | 0/1 | — | H/H | H/H | H, H | — |
| C | Si | 2 | N(i-Pr)Me | 0/1 | — | H/H | H/H | AMD, AMD | — |
| D | Se | 2 | Py | 0/1 | — | H/H | H/H | BDK | — |
| E | Cu | 1 | $N(i-Pr)_2$ | 0/1 | — | Me/H | H/H | PAMD | VTMS |
| F | Sc | 1 | NH(Allyl) | 1/1 | H/H | Me/H | H/H | N(Et)Me | — |
| G | La | 1 | $NMe_2$ | 1/1 | H/H | $Me_2NCH_2$/H | H/H | DMAP | — |
| H | Zr | 2 | $NEt_2$ | 2/0 | H/Me | H/Me | — | Cp, Cp | — |
| I | Hf | 3 | $NMe_2$ | 1/1 | H/H | H/H | H/H | DMAE | — |
| J | Nb | 2 | $NMe_2$ | 1/1 | H/H | H/Me | H/Me | Allyl, H, H | — |
| K | Ta | 1 | $PhNH_2$ | 0/2 | — | H/H | H/H | KIM | — |
| L | W | 2 | $Ph-NMe_2$ | 1/1 | H/H | H/H | H/H | t-Bu | — |
| M | Ni | 1 | $N(i-Pr)_2$ | 1/1 | H/H | H/Et | H/H | Pyrazo | Bz, CO |
| N | Ru | 2 | $N(c-Hx)_2$ | 2/1 | H/H | H/H | H/Et | $NO_3$ | — |
| O | Pt | 1 | PhOMe | 0/0 | — | H/Me | — | Me, Me, H | — |
| P | Pt | 2 | EtO | 2/1 | H/H, H/Me | H/Et | H/H | Cp, Me | — |

AMD = N,N'-dimethyl-methyl-amidinate;
PAMD = N,P-dimethyl-methylphosphoamidinate;
KIM = β-diketiminate;
BDK = β-diketonate;
DMAE = dimethylaminoethyl;
DMAP = dimethylaminopropyl.

In the above table, ligands separated by a comma denote that each ligand is present in that compound.

$(EDG\text{-}(CR^1R^2)_{y'}\text{---}CR^3\text{=}CR^4\text{---}(CR^5R^6)_{y''})_n M^{+m} L^1_{(m-n)} L^2_p$, wherein each $R^1$ and $R^2$ is independently chosen from H, $(C_1\text{-}C_6)$alkyl and EDG; $R^3$=H, $(C_1\text{-}C_6)$alkyl, EDG or EDG-$(CR^1R^2)_{y'}$; $R^4$=H or $(C_1\text{-}C_6)$alkyl; each $R^5$ and $R^6$ is independently chosen from H and $(C_1\text{-}C_6)$ alkyl; EDG is an electron donating group; M=a metal; $L^1$=an anionic ligand; $L^2$ is a neutral ligand; y'=0-6; y"=0-6; m=the valence of M; n=1-7; and p=0-3 and an organic solvent into the reactor using direct liquid injection; and depositing a film comprising the metal on the substrate.

2. The method of claim 1, wherein $L^1$ is chosen from hydride, halide, azide, alkyls, alkenyl, alkynyl, carbonyl, dialkylaminoalkyl, imino, hydrazido, phosphido, nitrosyl, nitryl, nitrate, nitrile, alkoxy, dialkylaminoalkoxy, siloxy, diketonates, ketoiminates, cyclopentadienyls, silyls, pyrazolates, guanidinates, phosphoguanidinates, amidinates, phosphoamidinates, amino, alkylamino, dialkylamino and alkoxyalkyldialkylamino.

3. The method of claim 1 wherein EDG comprises one or more of oxygen, phosphorus, sulfur, nitrogen, alkenes, alkynes and aryl groups.

4. The method of claim 1 wherein M is chosen from a Group 2 to Group 16 metal.

5. A method of depositing a film comprising the steps of:
providing a substrate in a vapor deposition reactor; conveying as a first precursor an organometallic compound of the formula $(EDG\text{-}(CR^1R^2)_{y'}\text{---}CR^3\text{=}CR^4\text{---}(CR^5R^6)_{y''})_n M^{+m} L^1_{(m-n)} L^2_p$, wherein each $R^1$ and $R^2$ is independently chosen from H, $(C_1\text{-}C_6)$alkyl and EDG; $R^3$=H, $(C_1\text{-}C_6)$alkyl, EDG or EDG-$(CR^1R^2)_{y'}$; $R^4$=H or $(C_1\text{-}C_6)$alkyl; each $R^5$ and $R^6$ is independently chosen from H and $(C_1\text{-}C_6)$ alkyl; EDG is an electron donating group; M=a metal; $L^1$=an anionic ligand; $L^2$ is a neutral ligand; y'=0-6; y"=0-6; m=the valence of M; n=1-7; and p=0-3 in a gaseous form to the reactor; chemisorbing the first precursor compound on the surface of the substrate; removing any non-chemisorbed first precursor compound from the reactor; conveying a second precursor in a gaseous form to the reactor; reacting the first and second precursors to form a film on the substrate; and removing any unreacted second precursor.

6. The method of claim 5, wherein the second precursor is chosen from oxygen, ozone, water, peroxide, alcohols, nitrous oxide and ammonia.

7. The method of claim 5, wherein $L^1$ is chosen from hydride, halide, azide, alkyls, alkenyl, alkynyl, carbonyl, dialkylaminoalkyl, imino, hydrazido, phosphido, nitrosyl, nitryl, nitrate, nitrile, alkoxy, dialkylaminoalkoxy, siloxy, diketonates, ketoiminates, cyclopentadienyls, silyls, pyrazolates, guanidinates, phosphoguanidinates, amidinates, phosphoamidinates, amino, alkylamino, dialkylamino and alkoxyalkyldialkylamino.

8. The method of claim 5, wherein EDG comprises one or more of oxygen, phosphorus, sulfur, nitrogen, alkenes, alkynes and aryl groups.

9. The method of claim 5, wherein M is chosen from a Group 2 to Group 16 metal.

\* \* \* \* \*